United States Patent
Zeng

(10) Patent No.: US 12,409,033 B2
(45) Date of Patent: Sep. 9, 2025

(54) AXISYMMETRIC ADJUSTABLE DEVICE FOR TREATING MITRAL REGURGITATION

(71) Applicant: Edwards Lifesciences Corporation, Irvine, CA (US)

(72) Inventor: Qinggang Zeng, Mission Viejo, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 1089 days.

(21) Appl. No.: 17/378,521

(22) Filed: Jul. 16, 2021

(65) Prior Publication Data

US 2021/0338427 A1    Nov. 4, 2021

Related U.S. Application Data

(63) Continuation of application No. 16/121,507, filed on Sep. 4, 2018, now Pat. No. 11,065,117.

(60) Provisional application No. 62/555,863, filed on Sep. 8, 2017.

(51) Int. Cl.
   *A61F 2/24*    (2006.01)

(52) U.S. Cl.
   CPC .......... *A61F 2/2445* (2013.01); *A61F 2/2454* (2013.01); *A61F 2/246* (2013.01); *A61F 2/2466* (2013.01); *A61F 2210/0014* (2013.01); *A61F 2220/0008* (2013.01); *A61F 2220/0025* (2013.01); *A61F 2230/0008* (2013.01);
   (Continued)

(58) Field of Classification Search
   CPC ...... A61F 2/2445; A61F 2/2454; A61F 2/246; A61F 2/2466; A61F 2210/0014; A61F 2220/0008; A61F 2220/0025; A61F 2230/0008; A61F 2230/0069; A61F 2250/0098
   See application file for complete search history.

(56) References Cited

U.S. PATENT DOCUMENTS

| 3,874,388 A | 4/1975 | King et al. |
| 4,340,091 A | 7/1982 | Skelton et al. |
| 4,506,669 A | 3/1985 | Blake, III |

(Continued)

FOREIGN PATENT DOCUMENTS

| CN | 1142351 A | 2/1997 |
| CN | 106175845 A | 12/2016 |

(Continued)

OTHER PUBLICATIONS

Al Zaibag et al., "Percutaneous Balloon Valvotomy in Tricuspid Stenosis", British Heart Journal, vol. 57, No. 1, Jan. 1987.

(Continued)

*Primary Examiner* — Jerrah Edwards
*Assistant Examiner* — Jose H. Trevino, III
(74) *Attorney, Agent, or Firm* — Anya Adams

(57) ABSTRACT

A prosthetic device for treating a native valve of a heart includes a sealing element and an anchoring element. The sealing element comprises a braided mesh material. The sealing element is dimensioned to be deployed at the native valve. The sealing element is configured to both be radially expanded and radially reduced while at a position between the native valve leaflets. The anchoring element is coupled to the sealing element and is configured to support the sealing element between the native valve leaflets.

7 Claims, 7 Drawing Sheets

(52) U.S. Cl.
CPC ............... *A61F 2230/0069* (2013.01); *A61F 2250/0098* (2013.01)

(56) References Cited

U.S. PATENT DOCUMENTS

| | | | |
|---|---|---|---|
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 8,968,395 B2 | 3/2015 | Hauser et al. |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,414,918 B2 | 8/2016 | Chau et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,610,163 B2 | 4/2017 | Khairkhahan et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |

(56) References Cited

U.S. PATENT DOCUMENTS

| | | |
|---|---|---|
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,575,841 B1 | 3/2020 | Paulos |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251177 A1 | 11/2005 | Saadat et al. |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0058871 A1 | 3/2006 | Zakay et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0282429 A1 | 12/2007 | Hauser et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0043382 A1 | 2/2009 | Maurer et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |

(56) References Cited

U.S. PATENT DOCUMENTS

| | | |
|---|---|---|
| 2014/0222136 A1 | 8/2014 | Geist et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0112429 A1 | 4/2015 | Khairkhahan et al. |
| 2015/0119981 A1 | 4/2015 | Khairkhahan et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008129 A1 | 1/2016 | Siegel |
| 2016/0008131 A1 | 1/2016 | Christianson et al. |
| 2016/0022970 A1 | 1/2016 | Forcucci et al. |
| 2016/0038280 A1* | 2/2016 | Morriss ............ A61F 2/2436 623/2.18 |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0166382 A1 | 6/2016 | Nguyen |
| 2016/0174979 A1 | 6/2016 | Wei |
| 2016/0174981 A1 | 6/2016 | Fago et al. |
| 2016/0199181 A1 | 7/2016 | Kramer |
| 2016/0242906 A1 | 8/2016 | Morriss et al. |
| 2016/0287387 A1 | 10/2016 | Wei |
| 2016/0302811 A1 | 10/2016 | Rodriguez-Navarro et al. |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0071487 A1 | 3/2018 | Khuu et al. |
| 2018/0078271 A1 | 3/2018 | Thrasher, III |
| 2018/0078361 A1 | 3/2018 | Naor et al. |
| 2018/0092661 A1 | 4/2018 | Prabhu |
| 2018/0126119 A1 | 5/2018 | McNiven et al. |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0352717 A1 | 11/2020 | Kheradvar et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |

(56) References Cited

U.S. PATENT DOCUMENTS

| | | |
|---|---|---|
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361238 A1 | 11/2021 | Bak-Boychuk et al. |
| 2021/0361416 A1 | 11/2021 | Stearns |
| 2021/0361422 A1 | 11/2021 | Gross et al. |
| 2021/0361428 A1 | 11/2021 | Dixon |
| 2021/0378818 A1 | 12/2021 | Manash et al. |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0296248 A1 | 9/2022 | Abunassar et al. |
| 2022/0313433 A1 | 10/2022 | Ma et al. |
| 2023/0014540 A1 | 1/2023 | Metchik et al. |
| 2023/0149170 A1 | 5/2023 | Giese et al. |
| 2023/0218291 A1 | 7/2023 | Zarbatany et al. |
| 2023/0270549 A1 | 8/2023 | Guidotti et al. |
| 2024/0148505 A1 | 5/2024 | Datta et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2006032051 A2 | 3/2006 |
| WO | 2014064694 A2 | 5/2014 |
| WO | 2016183485 A1 | 11/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Batista RJ et al., "Partial left ventriculectomy to treat end-stage heart disease", Ann Thorac Surg., vol. 64, Issue-3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.

Fucci et al., "Improved results with mitral valve repair using new surgical techniques", Eur J Cardiothorac Surg. 1995;Issue 9, vol. 11, pp. 621-626.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

Lawrence, Jr., et al., "Percutaneous Endovascular Graft: Experimental Evaluation", Cardiovascular Radiology 163, pp. 357-360, May 1987.

Maisano F et al., 'The edge-to-edge technique: a simplified method to correct mitral insufficiency', Eur J Cardiothorac Surg., vol. 13, Issue-3, pp. 240-245, Mar. 1998.

Pavcnik, M.D., Ph.D., Dusan, et al. "Development and Initial Experimental Evaluation of a Prosthetic Aortic Valve for Transcatheter Placement," Cardiovascular Radiology 1992; 183: 151-154.

(56) References Cited

OTHER PUBLICATIONS

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Reul RM et al., "Mitral valve reconstruction for mitral insufficiency", Prog Cardiovasc Dis., vol. 39, Issue-6, May-Jun. 1997.

Rosch, M.D., Josef, "The Birth, Early Years and Future of Interventional Radiology," J Vasc Interv Radiol 2003; 14:841-853.

Ross, D.N, "Aortic Valve Surgery", Surgery of the Aortic Valves, Guy's Hospital, London, pp. 192-197.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, @ 1994, 1990, pp. 803-815.

Uchida et al., "Modifications of Gianturco Expandable Wire Stents", Technical Note, American Roentgen Ray Society, pp. 1185-1187, May 1988.

Umaña JP et al., Bow-tie' mitral valve repair: an adjuvant technique for ischemic mitral regurgitation, Ann Thorac Surg., vol. 66, Issue-6, pp. 1640-1646, Nov. 1998.

"Urban, Philip MD, ""Coronary Artery Stenting"", pp. 5-47, @ 1991, ISBN: 2-88049-054-5, Editions Medecine et Hygiene, Geneva, Switzerland."

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Wheatley, David J., "Valve Prosthesis", Rob & Smith's Operative Surgery, pp. 415-424, 1986.

Grasso et al., "The PASCAL transcatheter mitral valve repair system for the treatment ofanother piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.

\* cited by examiner

FIG. 3A  FIG. 3B  FIG. 3C  FIG. 3D
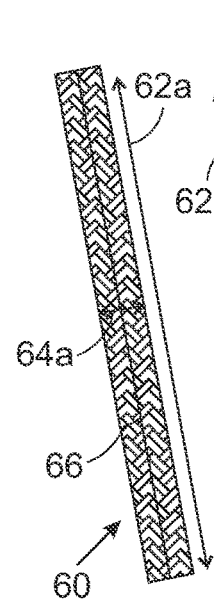 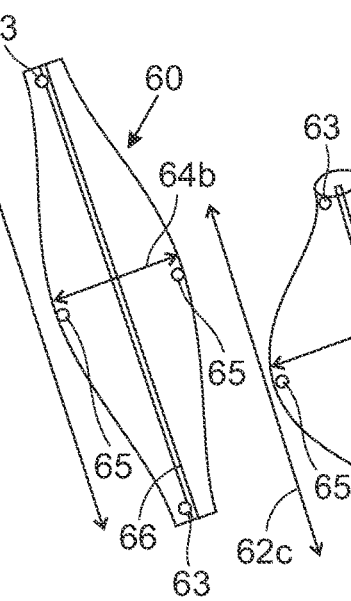 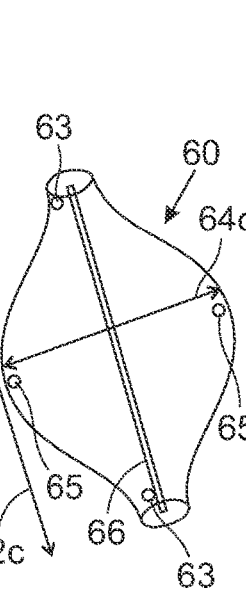 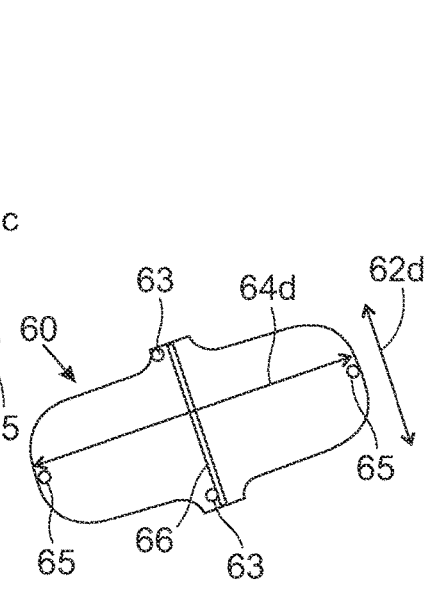
FIG. 3E  FIG. 3F  FIG. 3G  FIG. 3H
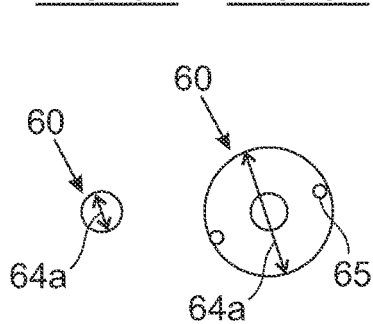 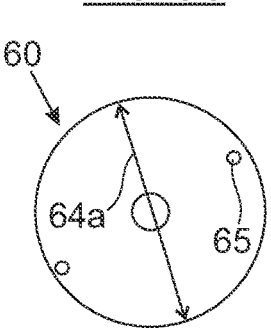 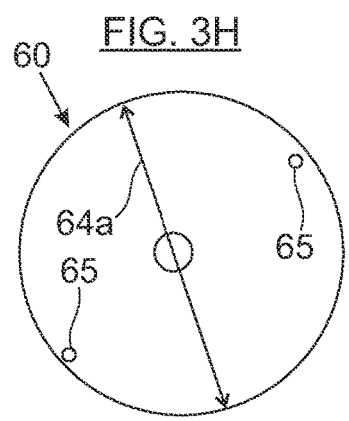

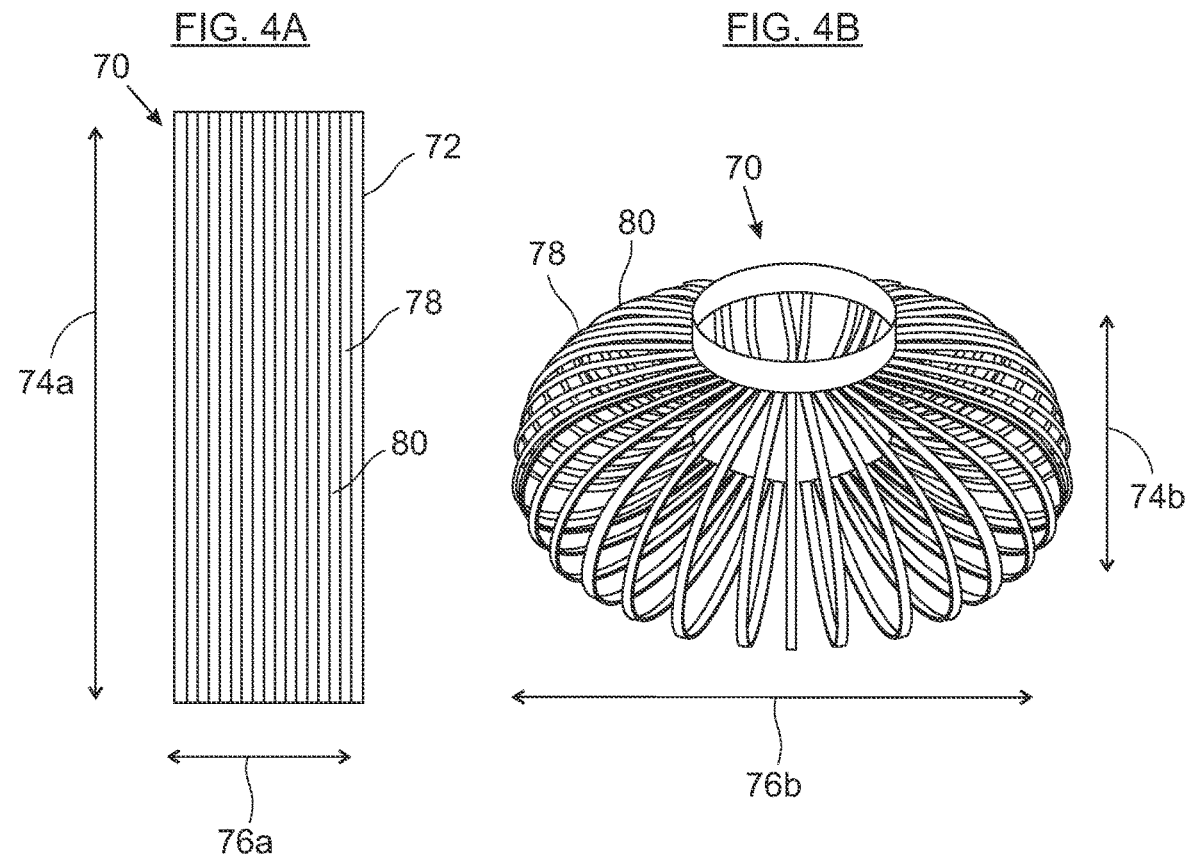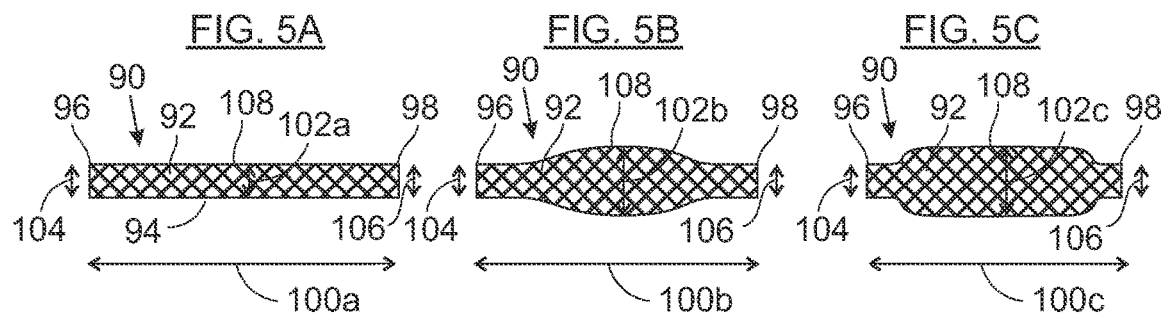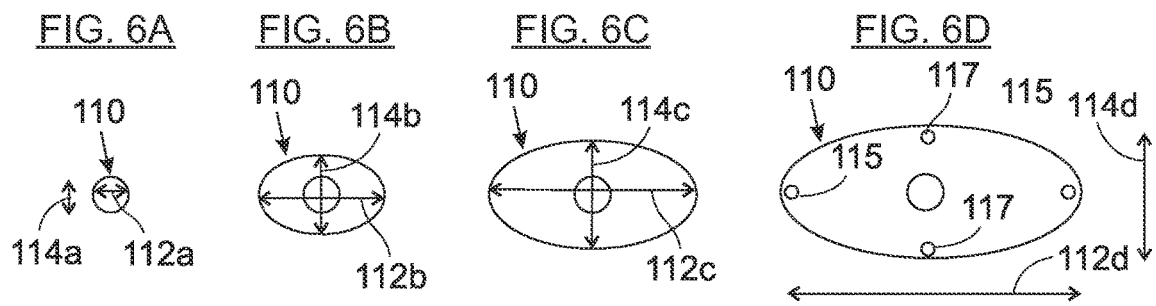

AXISYMMETRIC ADJUSTABLE DEVICE FOR TREATING MITRAL REGURGITATION

RELATED PATENT APPLICATIONS

This patent application is a continuation of U.S. patent application Ser. No. 16/121,507, filed on Sep. 4, 2018, which claims priority to U.S. Provisional Application No. 62/555,863, filed Sep. 8, 2017, and which is related to co-pending U.S. patent application Ser. No. 16/112,388, filed Aug. 24, 2018 and entitled "Transcatheter Device for Treating Mitral Regurgitation," the disclosures of all of these are incorporated by reference herein in their entireties for all purposes.

FIELD OF THE INVENTION

The present invention relates to the repair of heart valves, and, more particularly, to methods and apparatuses for the repair of heart valves by positioning a device between valve leaflets to improve valve closure.

BACKGROUND OF THE INVENTION

In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves separate the chambers of the heart, and are each mounted in an annulus therebetween. The annuluses comprise dense fibrous rings attached either directly or indirectly to the atrial and ventricular muscle fibers. The leaflets are flexible collagenous structures that are attached to and extend inward from the annuluses to meet at coapting edges. The aortic, tricuspid, and pulmonary valves usually have three leaflets, while the mitral valve usually has two leaflets.

The operation of the heart, and thus the patient's health, may be seriously impaired if any of the heart valves is not functioning properly. Various problems can develop with heart valves for a number of clinical reasons. Stenosis in heart valves is a condition in which the valves do not open properly. Insufficiency is a condition which a valve does not close properly. Repair or replacement of the aortic or mitral valves are most common because they reside in the left side of the heart where pressures and stresses are the greatest. In a valve replacement operation, a replacement prosthetic valve is implanted into the native valve annulus, which may involve excision of the native valve leaflets.

In many patients who suffer from valve dysfunction, surgical or percutaneous repair (i.e., "valvuloplasty") is a desirable alternative to valve replacement. Remodeling of the valve annulus (i.e., "annuloplasty") is central to many reconstructive valvuloplasty procedures. Remodeling of the valve annulus is typically accomplished by implantation of a prosthetic ring (i.e. "annuloplasty ring") to stabilize the annulus and to correct or prevent valvular insufficiency that may result from a dysfunction of the valve annulus. Annuloplasty rings are typically constructed of a resilient core covered with a fabric sewing ring. Annuloplasty procedures are performed not only to repair damaged or diseased annuli, but may also be performed in conjunction with other procedures, such as leaflet repair.

Heart valves may lose their ability to close properly due to dilation of an annulus around the valve or a flaccid, prolapsed leaflet. The leaflets may also have shrunk due to disease, such as rheumatic disease, thereby leaving a gap in the valve between the leaflets. The inability of the heart valve to close will cause blood to leak backwards (opposite to the normal flow of blood), commonly referred to as regurgitation. Common examples of such regurgitation include mitral valve regurgitation (i.e., leakage of blood through the mitral valve and back into the left atrium) and aortic valve regurgitation (i.e., leakage through the aortic valve back into the left ventricle). Regurgitation may seriously impair the function of the heart since more blood will have to be pumped through the regurgitating valve to maintain adequate circulation.

Heart valve regurgitation decreases the efficiency of the heart, reduces blood circulation, and adds stress to the heart. In early stages, heart valve regurgitation leaves a person fatigued and short of breath. If left unchecked, the problem can lead to congestive heart failure, arrhythmias, or death.

Mitral valve regurgitation may be caused by dysfunction of the mitral valve structure, such as may result from direct injury to the mitral valve leaflets. Such regurgitation can be caused by changes in the shape of the mitral valve annulus, damage to the posterior and/or anterior leaflets, and/or damage to the chordae tendinae. In such regurgitation, the anterior and posterior leaflets no longer coapt together properly to seal the valve, so that instead of the anterior and posterior leaflets coapting to fully close the mitral valve annulus during systole, an opening remains between the edges of the anterior and posterior leaflets.

Various methods of mitral valve repair are known in the art. Implantation of an annuloplasty ring, typically around the posterior aspect of the mitral valve, has proven successful in a number of cases. Such annuloplasty rings reshape the surrounding annulus, which can lead to proper coaptation of the native leaflets. Another repair technique for the mitral valve is known as a "bow-tie" repair, which involves suturing the anterior and posterior leaflets together in edge-to-edge fashion toward the middle of the leaflets, causing blood to flow through the two side openings thus formed. This process was originally developed by Dr. Ottavio Alfieri, and involved placing the patient on extracorporeal bypass in order to access and suture the mitral valve leaflets. Later adaptations of the bow-tie technique involved beating-heart repairs using percutaneous methods, such using a catheter to install suture or a clip to secure the opposing leaflets together.

Another approach to repairing a native valve having non-coapting leaflets, including mitral and aortic valves, involves inserting a device between the leaflets, with the device being sized and positioned to block the gap between the otherwise non-coapting leaflets. Examples of such repair devices and techniques are disclosed in U.S. Pat. No. 8,968,395 to Hauser et al. and U.S. Patent Pub. No. 2009/0043382 for Maurer et al. These disclose devices which include an anchor deployed in the lower ventricle which secures a blocking device within the mitral valve annulus.

There is presently a need for an improved means for performing heart valve repair. The current invention fulfills this need.

SUMMARY OF THE INVENTION

The present invention provides a number of devices and methods for improving valve function. The devices and methods herein reduce or eliminate valve regurgitation without interfering with normal valve function, i.e., not impeding the natural motion of the leaflets, chordae tendinae, or papillary muscles.

It should be understood that each of the sealing elements disclosed herein can be used with any and all of the anchor elements disclosed herein, even though the specific combination of sealing element with anchor elements may not be explicitly shown in the figures herein. In other words, based on the explanation of the particular device, one of skill in the art should have little trouble combining the features of certain of two such devices. Therefore, it should be understood that many of the sealing and anchor elements are interchangeable, and the invention covers all permutations thereof. Moreover, each of the sealing elements disclosed herein may be used alone or in combination with other anchor devices, and each of the anchor elements disclosed herein can be used alone or in combination with other implant devices, such as anchor and sealing elements disclosed in U.S. patent application Ser. No. 16/112,388, filed Aug. 24, 2018 and entitled "Transcatheter Device for Treating Mitral Regurgitation."

The devices of the present invention can be utilized in standard open surgical procedures, minimally-invasive procedures, or percutaneous procedures. In one embodiment the devices can be delivered through an open chest, e.g., transapically or transatrially. In another embodiment, the devices can be introduced through an incision performed over the roof of the left atrium. In yet another embodiment the devices can be delivered into the left ventricle through the right chest via a thoracscope, which may be performed transapically. The devices can also be delivered percutaneously, such as via a catheter or catheters into the patient's arterial system (e.g. through the femoral or brachial arteries).

Advantages of the device include a low delivery profile, which is conducive to minimally-invasive and percutaneous delivery methods. The device is configured to interact properly with the native leaflets, ventricle, atrial, and subvalvular apparatus. The device preserves rather than obstructs the mobility and dynamic motion of the native leaflets (except as necessary for proper coaptation). The native leaflets and chordae tendinae are preserved, and continue to operate (including opposing the systolic closing pressure). The subvalvular process and left ventricle coordination are thus preserved. The device may be configured so that it does not expand the native mitral valve leaflets or annulus outward, so that left ventricular outflow tract (LVOT) impingement/obstruction should not be a concern. The shape and low profile of the sealing element minimizes flow resistance during diastole, and there are no areas of stasis created by the device. A single device can be applicable to a wide range of valve sizes.

The device may be applicable to numerous mitral valve regurgitation conditions, including those caused by leaflet prolapse with varying amounts of annular dilatation (type I), focal leaflet prolapse (type II), and leaflet tethering (type IIIb).

Embodiments of the present disclosure provide devices and methods for improving the function of a defective heart valve, such as a mitral valve. The devices and methods disclosed herein are desirably delivered into a subject's heart using percutaneous or minimally invasive surgical methods. Accordingly, desirable delivery methods described herein may not require extracorporeal circulation (e.g., blood from a subject's circulation being routed outside the body to have a process applied to and then, returned of the subject's circulation). For example, in one embodiment, a delivery catheter (or similar delivery device) is inserted through an incision in the chest wall and then through the cardiac tissue (e.g., through the apex of the heart) into a chamber of the patient's beating heart. The delivery catheter can allow a prosthetic device to be delivered into the heart in a collapsed configuration and then expanded within the heart for treating a defective heart valve. Because delivery methods may not require extracorporeal circulation, complications can be greatly reduced as compared with traditional open-heart surgery.

An embodiment of the invention for treating a mitral valve is a device that includes an expandable prosthetic sealing member having an axisymmetrical top profile (or an elongated or elliptical top profile) when expanded, the sealing member shaped when expanded for contacting the leaflets of the mitral valve. The device also includes an anchoring member coupled to the sealing member and configured to secure the sealing member at a desired position between the mitral valve leaflets. The anchor member may have an axisymmetrical top profile. The sealing member and anchoring member may be radially collapsible and radially expandable, which may permit the device to be delivered and deployed via a catheter.

Various anchoring elements are within the scope of the invention. Many of the anchoring elements may be axisymmetric, which is to say symmetrical about an axis running from a lower (e.g., ventricular) end to an upper (e.g., atrial) end. In one embodiment, an anchor element may have an upper portion configured to extend around a mitral valve annulus and contact atrial tissue adjacent the mitral valve annulus, a lower portion configured to extend around native valve leaflets and engage ventricular tissue adjacent the mitral valve annulus without interfering with the movement of the mitral valve leaflets, and a central portion configured to support the sealing member. The anchor element upper portion may have an upper portion may have a plurality of radially-extending arms to engage heart tissue such as atrial tissue adjacent a mitral valve. The lower portion may have a plurality of radially-extending arms to engage heart tissue such as ventricular tissue adjacent a mitral valve, and may be dimensioned such when the lower portion is deployed the native valve leaflets can open and close as the heart beats with limited or no interference from the lower portion. In one embodiment of the device, the native valve leaflets are unrestricted in their opening and closing by any and all portions of the device except for the sealing element, which engages the native valve leaflets during systole to form a seal between the native leaflets and thereby prevent mitral valve regurgitation.

An anchoring member according to the invention may be configured so that the anchoring member does not expand the native mitral valve annulus, because such annulus expansion might otherwise cause reduction in valve efficiency. For example, the anchoring member may be configured so it does not subject the native mitral valve annulus to radially-expansive forces. The anchoring member may be configured so that the lower anchor portion presses upward against the native valve annulus while the upper anchor portion presses downward against the native valve annulus, so that tissue of the native valve annulus is held between the lower anchor portion and the upper anchor portion but the annulus is not subjected to radially-expansive forces from the anchoring member. Such embodiments may even prevent further annulus expansion by securing the annulus between the opposing anchor portions.

An anchoring member according to the invention may be self-expandable, such as via construction of a memory material such as nitinol. The anchoring member may alternatively be formed of other materials, such as stainless steel or cobalt chromium.

Another anchor element according to the invention is configured for deployment in a single heart chamber such as the atrium, with only the sealing element extending out of the chamber and into the heart valve and annulus. For example, an anchor element may have a plurality of upper arms configured to engage the upper portion of the heart chamber, and a plurality of lower arms configured to engage the lower portion of that same heart chamber. The upper or lower arms, or other structure of the anchor element, may have curves configured to act as shock absorbers to permit the anchor element to flex responsive to movements of the heart chamber as the heart beats.

A sealing element according to the invention is configured to be introduced in a radially collapsed but lengthened configuration, and then be shortened and radially expanded to a desired shape for improving valve function. The sealing element may be axisymmetric or elongated (e.g., elliptical) in top profile, and may dimensioned to be deployed in an annulus of a native valve (e.g., mitral valve) of a heart at a position between native valve leaflets to contact the native valve leaflets during ventricular systole to create a seal to prevent regurgitation of blood from the ventricle to the atrium, while permitting the native valve leaflets to open and close as the heart beats. The sealing element may have an upper end, a lower end, an anterior surface, and a posterior surface. The anterior surface may be configured to coapt with a mitral valve anterior leaflet, and the posterior surface may configured to coapt with a mitral valve posterior leaflet. The sealing element may have a mesh support frame with a delivery configuration where the mesh support frame is substantially tubular with a delivery diameter, and an expanded configuration where the mesh support frame is radially expanded with an expanded central diameter at a center portion thereof while end portions of the mesh support frame remain in the delivery diameter. The expanded central diameter may be at least twice the delivery diameter, at least three times the delivery diameter, at least four times the delivery diameter, at least five times the delivery diameter, etc. A covering may cover the mesh support frame to prevent the passage of blood therethrough. The sealing element in the expanded configuration may comprise an axisymmetrical, elongated, or elliptical top profile.

A sealing element outer covering may preferably wrap around the exterior and/or interior of the central anchor portion or any other support structure for the sealing element, so that the wireform elements of the central anchor portion or other support frame are covered and/or encapsulated by the sealing element in order to prevent the native valve leaflets from contacting any frame elements of the central anchor portion.

A system for treating a mitral valve according to an embodiment of the invention may have a delivery catheter, an anchor member, and a prosthetic sealing member. The anchoring member may be self-expanding and/or axisymmetric, and may have a plurality of radially-extendable arms for engaging heart tissue. The sealing member may be adapted for plugging a gap between the leaflets of the mitral valve and reducing regurgitation. The prosthetic sealing member may have a collapsed state and an expanded state, where in the collapsed state the sealing member is longer and thinner than in the expanded state. The sealing member may have an outer surface formed with biological tissue. The elongated cross-sectional profile of the sealing member may be solid such that blood is forced to flow around the sealing member.

A method according to the invention for improving the function of a heart valve may involve advancing a distal end of a delivery catheter to a position at a mitral or other heart valve of a patient, wherein within the distal end is a prosthetic device having an anchor member and a sealing member. The sealing member may be configured to expand into a configuration to reduce regurgitation through the mitral valve. The anchor member may have an upper portion configured to expand into engagement with atrial tissue, a central portion configured to expand to support the sealing member, and a lower portion configured to expand into engagement with ventricular tissue. The anchor member may have an upper portion to engage the upper portion of the heart chamber, and a lower portion configured to engage the lower portion of that same heart chamber. The anchor member may be self-expandable, and/or formed of memory material, and may be mounted in a compressed state within a distal end of the delivery catheter. The method may further include releasing the anchor member upper portion from the catheter at a position such that the anchor member upper portion engages desired heart tissue, releasing the sealing member from the catheter, and releasing the anchor member lower portion from the catheter at a position such that the anchor member lower portion engages desired heart tissue. This deployment procedure could be performed in different orders, such as releasing the anchor member lower portion first, then the sealing member, and then the upper portion; or releasing the sealing member before or after the release of the lower and upper anchor portions. After deployment of the anchor member portions and the sealing member, the sealing member should be positioned between leaflets of the mitral valve such that during systole the leaflets coapt against the sealing member. The length and width of the sealing member may be adjusted after initial deployment by a user to improve heart valve function. The device may be delivered and deployed using various delivery techniques, such as percutaneously or transapically to the mitral or other heart valve.

Methods of the invention may include advancing a distal end of a delivery catheter to a position at a heart valve (e.g., mitral valve) in a heart of a patient, wherein within the distal end is a prosthetic device having an anchor member and a sealing member, the sealing member being configured to expand into an axisymmetrical or elongated-and-symmetrical (e.g., elliptical) configuration to engage native mitral valve leaflets during systole while still allowing the native mitral valve leaflets to open and close as the heart beats; releasing the anchor member portion from the catheter at a position in the heart at or adjacent the native valve annulus to engage heart tissue and anchor the anchor member within the heart; releasing the sealing member from the catheter; radially expanding the sealing member, wherein the sealing member as it expands shortens in length while increasing in diameter, wherein the sealing member after expansion comprises an axisymmetrical or elongated/elliptical top profile. After release of the anchor member and the sealing member, the sealing member is positioned between leaflets of the mitral valve such that during systole the leaflets coapt against the sealing member and the leaflets can open and close as the heart beats.

The sealing member after expansion may have a circular top profile, or an elongated top profile (such as an elliptical top profile). The sealing member may be rotated about its central axis and with respect to the native valve annulus to a desired rotational position wherein the sealing member is aligned within the valve annulus with native valve features to improve valve leaflet coaptation against the sealing member. This rotation may be selectively performed by a user, and the user may also lock the sealing member at the desired rotational position. For an elongated sealing element, rotating the sealing member about its central axis may involve aligning a major axis of the sealing member to be substantially parallel (within 10 degrees) of a line between commissures of a mitral valve.

Deployment of the device may be performed responsive to feedback of valve performance monitoring and/or visualization techniques. For example, while expanding or rotating the sealing element, a user may monitor valve performance and set the final expansion configuration and/or rotational position of the sealing element in a configuration where valve performance is maximized based on the valve performance and/or visualization feedback.

The anchor member may comprise an upper portion and a lower portion. A central portion may be included, and configured to support the sealing member. In one embodiment, the upper portion is configured to expand into engagement with atrial tissue, and the lower portion is configured to expand into engagement with ventricular tissue. Methods for deploying it may include releasing the upper portion into engagement with atrial tissue, releasing the lower portion into engagement with ventricular tissue. In one embodiment, the upper portion is configured to expand into engagement with upper atrial tissue, and the lower portion is configured to expand into engagement with lower atrial tissue adjacent the native valve annulus. Methods for deploying it may include releasing the upper portion into engagement with upper atrial tissue, and releasing the lower portion into engagement with lower atrial tissue. Releasing the anchor member upper portion from the catheter may occur prior to, simultaneously with, or after releasing the anchor member lower portion from the catheter.

The device may be delivered using various approaches, including percutaneously or transapically through the subject's vasculature.

Other objects, features, and advantages of the present invention will become apparent from a consideration of the following detailed description.

BRIEF DESCRIPTION OF THE DRAWINGS

FIGS. 3A-3D depict side views of a sealing element in various stages of expansion according to an embodiment of the invention;

FIGS. 3E-3H depict top views of the sealing element in the various stages of expansion depicted in FIGS. 3A-3D;

FIGS. 4A-4B depict side and perspective views, respectively, of a slotted-tube sealing element frame in compressed and expanded configurations, respectively, according to an embodiment of the invention;

FIGS. 5A-5C depict side views of a braided mesh sealing element in various stages of expansion according to an embodiment of the invention;

FIGS. 6A-6D depict top views of a sealing element in various stages of expansion according to an embodiment of the invention;

DETAILED DESCRIPTION OF SEVERAL EMBODIMENTS

Figure 1:
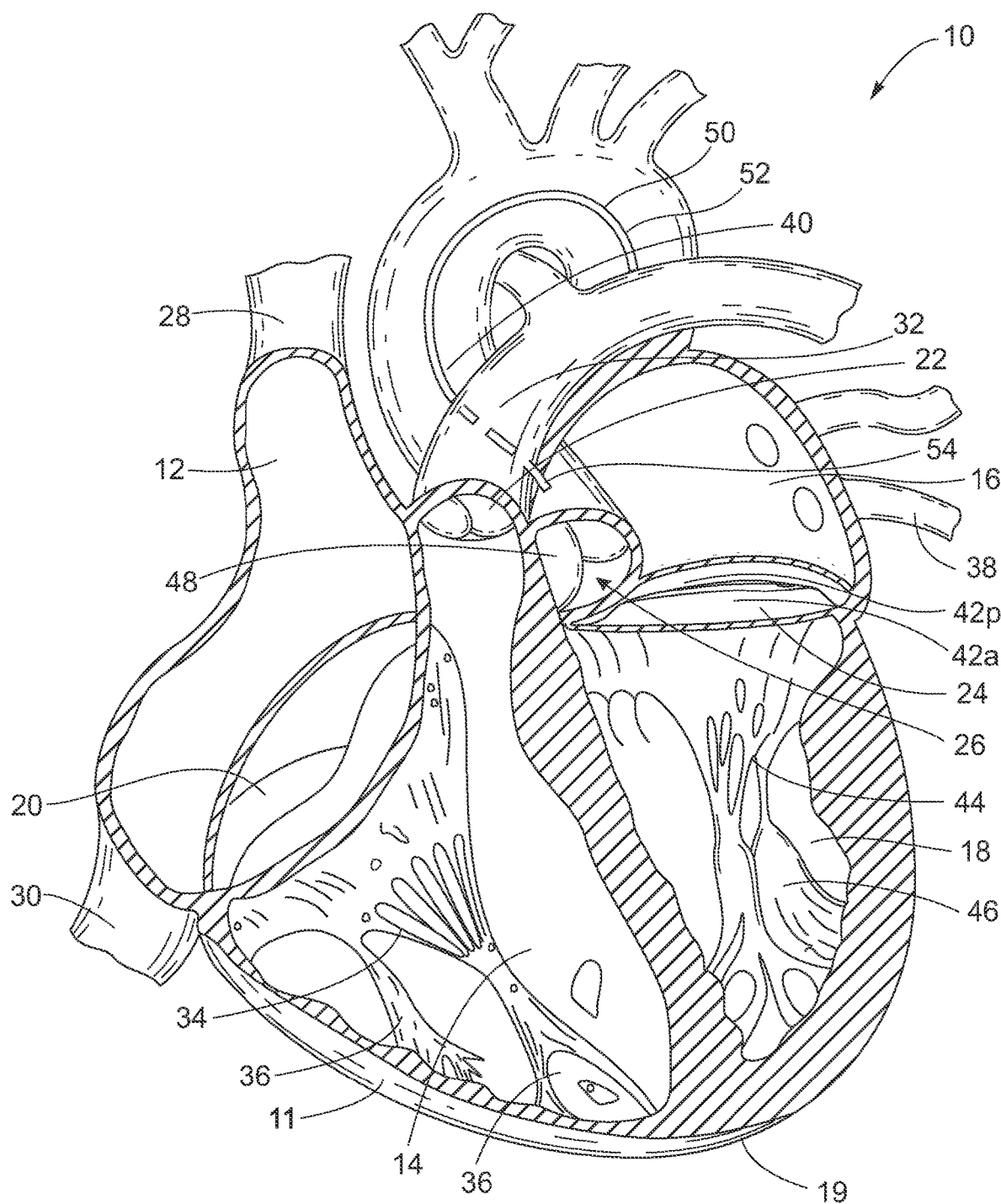
FIG. 1 is a cross-sectional view of a heart.

A cross-sectional view of a human heart 10 is depicted in FIG. 1. The heart 10 has a muscular heart wall 11, an apex 19, and four chambers: right atrium 12; right ventricle 14; left atrium 16; and left ventricle 18. Blood flow is controlled by four main valves: tricuspid valve 20; pulmonary valve 22; mitral valve 24; and aortic valve 26. Blood flows through the superior vena cava 28 and the inferior vena cava 30 into the right atrium 12 of the heart 10. The right atrium 12 pumps blood through the tricuspid valve 20 (in an open configuration) and into the right ventricle 14. The right ventricle 14 then pumps blood out through the pulmonary valve 22 and into the pulmonary artery 32 (which branches into arteries leading to the lungs), with the tricuspid valve 20 closed to prevent blood from flowing from the right ventricle 14 back into the right atrium. Free edges of leaflets of the tricuspid valve 20 are connected via the right ventricular chordae tendinae 34 to the right ventricular papillary muscles 36 in the right ventricle 14 for controlling the movements of the tricuspid valve 20.

After leaving the lungs, the oxygenated blood flows through the pulmonary veins 38 and enters the left atrium 16 of the heart 10. The mitral valve 24 controls blood flow between the left atrium 16 and the left ventricle 18. The mitral valve 24 is closed during ventricular systole when blood is ejected from the left ventricle 18 into the aorta 40. Thereafter, the mitral valve 24 is opened to refill the left ventricle 18 with blood from the left atrium 16. Free edges of leaflets 42a, 42p of the mitral valve 24 are connected via the left ventricular chordae tendinae 44 to the left ventricular papillary muscles 46 in the left ventricle 18 for controlling the mitral valve 30. Blood from the left ventricle 18 is pumped through the aortic valve 26 into the aorta 40, which branches into arteries leading to all parts of the body except the lungs. The aortic valve 26 includes three leaflets 48 which open and close to control the flow of blood into the aorta 40 from the left ventricle 18 of the heart as it beats.

Figure 2A:
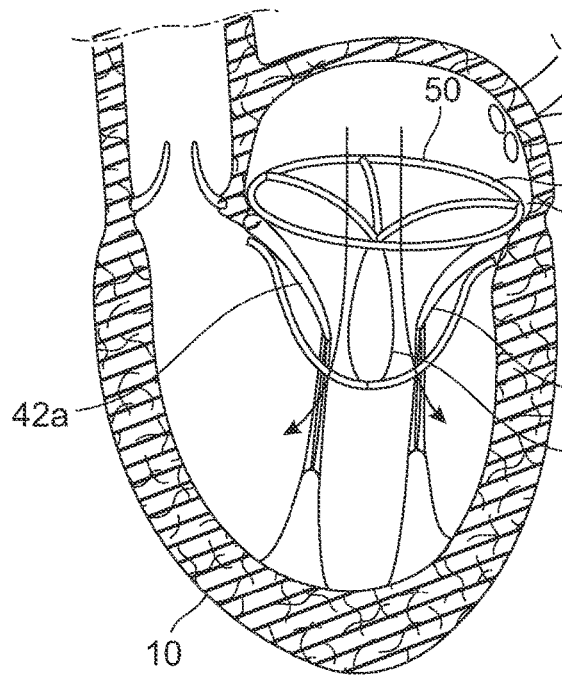
FIGS. 2A-2D depict side cross-sectional views of a heart with a repair device deployed therein according to an embodiment of the invention.
Figure 2B:
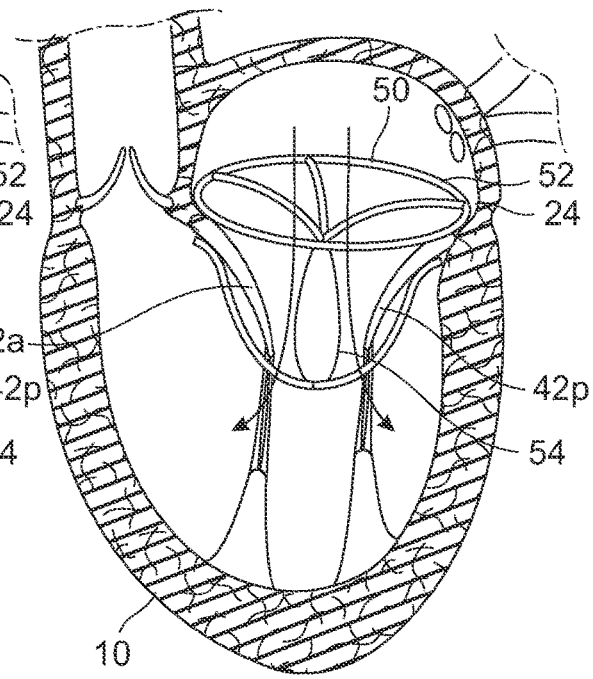
Figure 2C:
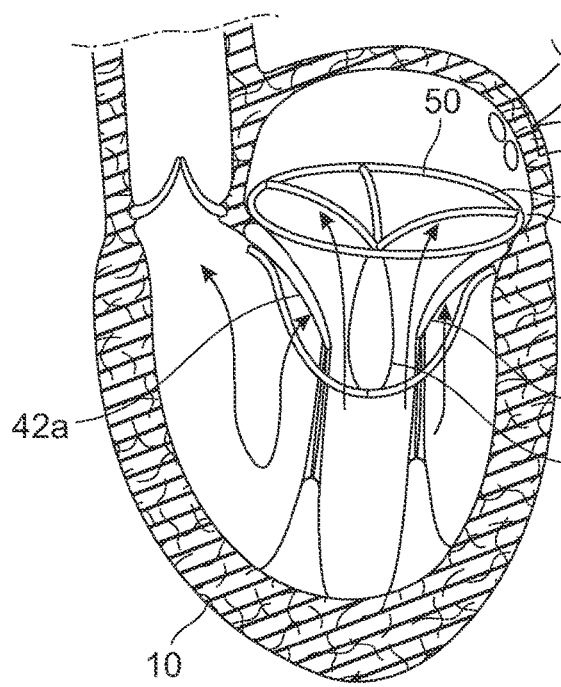
Figure 2D:
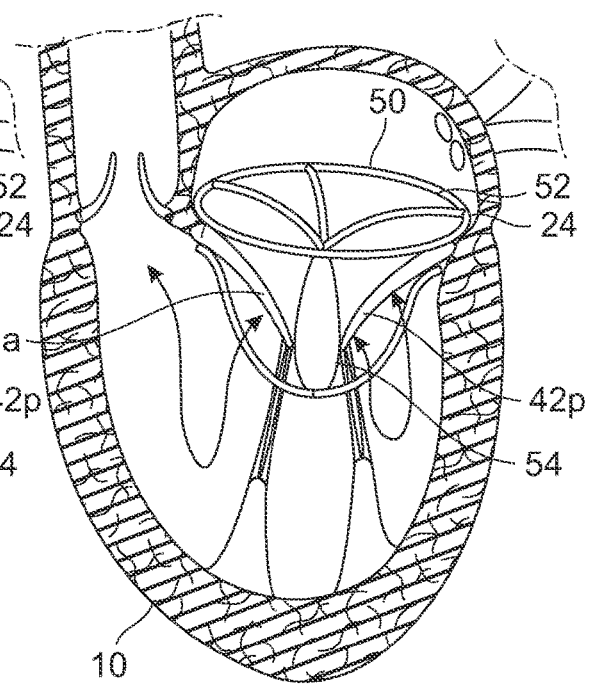

FIGS. 2A-2D depict a device 50 deployed in a native mitral valve 24 and mitral valve annulus 25 according to an embodiment of the invention. The device 50 has a support anchor 52 and a sealing element 54. The support anchor 52 may be configured to permit free movement of the native valve leaflets 42a, 42p. In FIG. 2A, the native mitral valve 24 is in early diastole, with the native leaflets 42a, 42p starting to open and permit blood to flow from the left atrium 16 to fill the left ventricle 18. In full diastole as depicted in FIG. 2B, the mitral valve leaflets 42a, 42p are fully open. In early systole as depicted in FIG. 2C, initial backward flow into the left atrium 16 pushes the mitral valve leaflets 42a, 42p back (upwards) and into engagement with each other and with the sealing element 54. In full systole as depicted in FIG. 2D, the native mitral valve leaflets 42a, 42p wrap tightly against the sealing element 54 under peak systolic pressure, effectively eliminating any regurgitation flow.

A sealing element 60 according to an embodiment of the invention is depicted in FIGS. 3A-3D and 3E-3H. The sealing element 60 has a fully compressed state, depicted in FIGS. 3A and 3E, which may be useful for delivery via a catheter and where the sealing element 60 may be substantially tubular and have an initial/delivery length 62a and an initial/delivery maximum diameter 64a. The sealing element 60 can be expanded by shortening the length 62b, 62c, thus forcing the sealing element maximum diameter 64a, 64b, to increase, as depicted in FIGS. 3B-3C and 3F-3G. The sealing element 60 can reach its deployed length 62d and deployed maximum diameter 64d, depicted in FIGS. 3D and 3H. A sealing element 60 according to the invention may have an initial/delivery length 62a of between 15-60 mm; 40-50 mm; 30-55 mm; etc. The sealing element 60 may have an initial/delivery maximum diameter 64a of between 0-10 mm; 5-8 mm; 6 mm; etc. The sealing element 60 according to the invention may have a deployed length 62a of between 20-45 mm; 25-35 mm; around 30 mm; etc., and a deployed maximum diameter 64a of between 5-40 mm; 10-30 mm; 15-25 mm; etc. The ratio of height/length to diameter may vary, depending on the particular application. Example ranges for height/length to diameter ratios are: 10:1, or 5:1, or 3:1, and ranges therebetween, during delivery; and 1:4, or 1:2, or 1:1, or 2:1, and ranges therebetween, at deployment. Note that each of these ratios and ranges for a particular sealing element dimension (e.g., delivery diameter, deployed diameter, delivery height/length, deployed height/length, etc.) may be combined with any and all of the other sealing element dimensions in accordance with the invention.

A sealing element and/or anchor element according to the invention may include radiopaque or other visualization markers to enhance user visualization of the device. For example, in the embodiment of FIGS. 3A-3F, radiopaque or other visualization markers 63, 65, are included. Markers 63 are positioned toward the ends of the sealing element, and can be used to visualize the height/length of the sealing element. Perimeter markers 65 are positioned toward the perimeter of the sealing element toward its widest point, and can be used to visualize the diameter of the sealing element. All markers can also be used to monitor the position of the sealing element.

The sealing element 60 may have an expansion control element 66, the length of which can be adjusted to thereby control the overall length and thereby the expansion of the sealing element. The sealing element 60 may preferably have a sealing surface (not shown), which may be in the form of an outer covering that prevents the passage of blood therethrough. The sealing surface may be supported by an expandable support frame (not shown). Note that in the embodiment depicted in FIGS. 3A-3D, the expansion control element 66 corresponds to the central axis of the sealing element 60, about which the sealing element 60 may be axisymmetric during deployment and after expansion.

An expandable support frame 70 in a so-called "slotted tube" configuration according to an embodiment of the invention is depicted in FIGS. 4A and 4B. As shown in FIG. 4A, in its compressed/delivery configuration the support frame 70 comprises a substantially cylindrical body 72, and a delivery length 74a and delivery maximum diameter 76a. The support frame 70 construction, with slits 78 between rib-like elements 80, permits the support frame 70 to be radially expanded, with the rib-like elements 80 bending outward, with the support frame 70 reaching a deployed length 74b and deployed maximum diameter 76b as depicted in FIG. 4B. Note that the deployed length 74b is less than the delivery length 74a, while the deployed maximum diameter 76b is greater than the delivery maximum diameter 76a. The delivery configuration is conducive to delivery via a catheter into a human heart. The addition of a sealing surface (not shown), such as in the form of an outer covering, to the support frame 70 will create a sealing element according to an embodiment of the invention. Expansion of the support frame 70 may be accomplished via mechanisms such as tethers, ratchets, etc., and/or may involve constructing the support frame 70 from shape-memory materials such as nitinol.

A support frame 90 according to an embodiment of the invention may include a braided mesh sleeve, depicted in FIGS. 5A-5C, where strands 92 (such as wires or other strand-like elements) are braided or otherwise formed into a mesh structure defining a generally tubular structure 94. The mesh structure may cause the frame 90 to radially expand when its length is compressed, and to radially reduce when its length is reduced (in similar fashion to contractible finger traps used as children's toys). The support frame 90 has a distal end 96 and proximal end 98, with a length 100a, 100b, 100c and maximum diameter 102a, 102b, 102c. The diameters 104, 106 of the distal end 96 and proximal end 98 may be generally fixed, so that this portion of the support frame 90 is prevented from appreciably radially expanding even as the maximum diameter expands. As the support frame 90 is reduced in length from its delivery length 100a to its deployed length 100c, the support frame 90 increases in maximum diameter from its delivery maximum diameter 102a to its deployed maximum diameter 102c. Note that, depending on how the support frame is formed (e.g., how the strands 92 are braided, the materials used, etc.), the central portion 108 of the support frame 90 may retain a substantially tubular shape even as the central portion 108 and support frame 90 are radially expanded. In other embodiments, the support frame 90 may form a more spherical shape, of even shapes having varying radial dimensions around a circumference of the frame 90. The addition of a sealing surface (not shown), such as in the form of an outer covering, to the support frame 90 will create a sealing element according to an embodiment of the invention. Expansion of the support frame 90 may be accomplished via mechanisms such as tethers, ratchets, etc., and/or may involve constructing the support frame 00 from shape-memory materials such as nitinol.

Support frames and sealing elements according to the invention may be configured to form non-circular profiles when viewed from the top. For example, in the embodiment of FIGS. 6A-6D, a sealing element 110 which may have side profiles during delivery and expansion similar to that depicted in FIGS. 3A-3D, but instead of having the circular top profiles as depicted in FIGS. 3E-3H instead forms an elongated/elliptical top profile when deployed, where a major diameter 112*d* is much larger than the minor diameter 114*d* when the sealing element 110 is fully expanded as depicted in FIG. 6D. Such a non-circular/elliptical sealing element may include radiopaque or other visualization markers 115, 117, e.g., positioned toward the sealing element perimeter and along/adjacent the major axis 115 and/or minor axis 117, via which a user can visualize not just the dimensions (major diameter and/or minor diameter) but also the rotational orientation of the sealing element about its central axis and with respect to the anchor element and/or native valve. During delivery, the maximum diameter may be between 0-10 mm; 5-8 mm; 6-7 mm; etc. The expanded minor diameter 114*d* may be between 5-20 mm; 10-15 mm; etc., and the expanded major diameter 112*d* may be between 10-40 mm; 15-40 mm; 20-30 mm; etc.

Figure 7A:
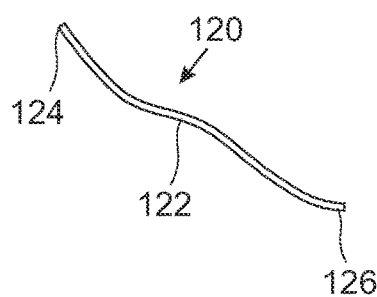
FIGS. 7A-7C depict perspective views of various mechanisms for controlling the expansion of sealing elements according to embodiments of the invention.

Expansion of sealing elements may be controlled via the use of various mechanisms. For example, as depicted in FIG. 7A, an internal tethering mechanism 120 may comprise a tether line 122 with a first end 124 that may be secured to an end of a support frame (not shown) and a second end 126 that may passed through an opposing end of the support frame. By pulling on the second end 126 and thereby shortening the length of the internal tether that lies within the support frame, the support frame is reduced in length and radially expanded. The internal tethering mechanism may include a lock, such as a knot, one-way lock, or other locking mechanism (not shown), at the opposing end of the support frame for securing the internal tether at the desired length that corresponds to the desired shape (i.e., maximum diameter/length) of the deployed sealing element. Such a tether may be used with any and all sealing elements and support frames of the invention, and may be particularly useful for sealing elements having self-expanding support frames where the tether acts to restrain and control expansion of the support frame.

Figure 7B:
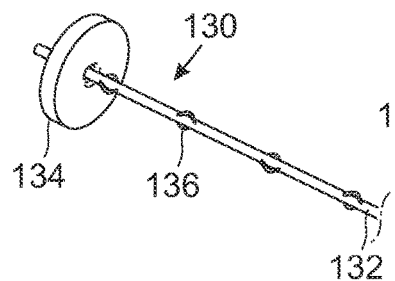

Expansion of a sealing element according to the invention may be controlled by a generally rigid rod 130 that resists both tension and compression, as depicted in FIG. 7B. A first end 132 of the rod 130 may be secured to a first end of a support frame (not shown), with the rod 130 passing through a locking mechanism 134 at a second end of the support frame with the second end 134 of the rod 130 on the far side of the locking mechanism from the first end 132. The rod 130 may include tooth-like elements 136 that are selectively engaged by the locking mechanism 134. For example, the locking mechanism 134 may permit the tooth-like elements to pass outwardly through the locking mechanism (as may be desired to shorten the rod 130 and thereby shorten and radially expand a support frame), but prevent the tooth-like elements from passing inwardly through the locking mechanism.

Another option for controlling expansion of sealing element is a linear screw mechanism 140, where an elongated screw 142 has a first end 144 secured to a first end of a support frame (not shown). A screw-receiving nut 146 is secured via extenders 148 to a second end of the support frame. Either the screw-receiving nut 146 or the screw first end 144 is rotatably secured to the support frame, permitting rotation of the screw with respect to the screw-receiving nut which thereby advances/retracts the screw 142 through the screw-receiving nut 146 and thereby adjusts the length of the linear screw mechanism and the length/expansion of the support frame.

Figure 8A:
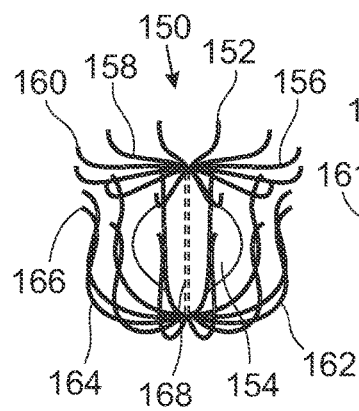
FIG. 8A depicts a perspective view of a device according to an embodiment of the invention.
Figures 8B, 8C:
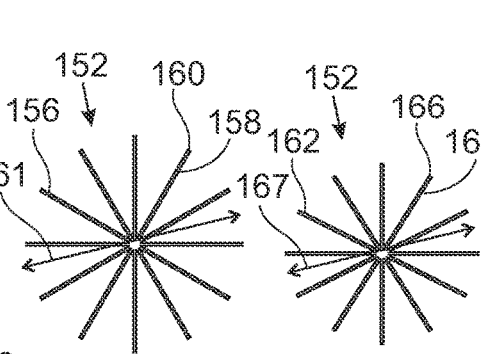
FIGS. 8B-8C depict top and bottom views, respectively, of an anchor according to an embodiment of the invention.
Figure 8D:
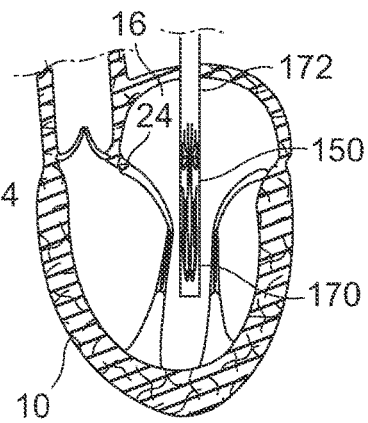
FIGS. 8D-8G depict side views of heart chambers with the device of FIG. 8A at various stages of deployment therein according to an embodiment of the invention.

FIG. 8A depicts a perspective view of a device 150 that is configured for deployment with portions secured in the atrium, ventricle, and valve annulus of a patient. An anchor element 152 anchors and supports a sealing element 154. The anchor element 152 has an atrial portion 156 with atrial arms 158 terminating in atrial arm distal ends 160, with the atrial arms 158 sized and shaped to extend across the lower portion of the atrium and engage the valvular annulus from the atrial side. A ventricular portion 162 has ventricular arms 164 terminating in ventricular arm distal ends 166. The ventricular arms 164 may be sized and shaped to extend around the "swing" area through which the native valve leaflets swing as the heart beats, so as not to engage against the native valve leaflets as the valve leaflets open and shut. The ventricular arms 164 curve around the leaflets swing area and then curve back upward to engage the valvular annulus from the ventricular side. Note that the anchor element 152 depicted when expanded in air or otherwise expanded in the absence of compressive forces (such as compressive forces that might be present when deployed in a heart) is axisymmetrical when viewed directly from above or below, as seen in FIGS. 8B-8C, so that during deployment the surgeon or other user does not have to worry about whether the anchor element 152 of the device 150 is rotated around its central axis to a proper deployment position with respect to the native valve and valve annulus. In the particular embodiment depicted, the expanded diameter 161 of the upper anchor element 156 is slightly larger than the expanded diameter 167 of the lower anchor element 162, although the invention is not limited to this configuration. The lower anchor expanded diameter 167 may be between 25 and 60 mm, and the upper anchor expanded diameter 161 may be between 30 and 70 mm. Note that when expanded in an actual heart, the individual arms 158, 164 of the upper and lower anchor elements 156, 162 will be compressed or otherwise distorted by their interaction with the heart tissue, so that each arm may be contorted by the heart tissue into a shape slightly different from the shapes of other arms.

Figure 7C:
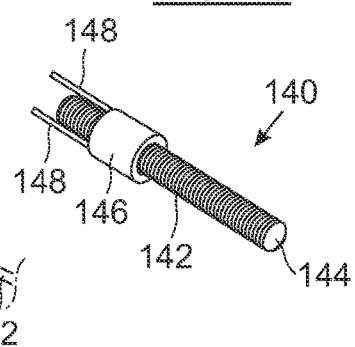

The anchor element 152 of FIG. 8A includes a central portion 168 which passes through the sealing element 154. The central portion 168 may be configured to act as a support frame for the sealing element, and/or may be configured to be shortened (e.g., by incorporating shortening mechanisms such as those in FIGS. 7A-7C) in order to effectuate shortening and thereby expansion of the sealing element 154. In the particular embodiment depicted, the sealing element central portion 168 surrounds an axis of the sealing element 154 and of the anchor element 152. Note that the sealing element 154 in top profile (i.e., about its central axis) may be axisymmetric (e.g., circular) as in FIGS. 3E-H, or may be non-circular (e.g., elliptical) as in FIGS. 6A-6D. The sealing element 154, especially if it is non-circular/elliptical in top profile, may be configured for axial rotation (selective or responsive to body operation such as blood flow/valve operation) with respect to the anchor element 152, and a lock may be provided that can be activated to prevent further rotation of the sealing element 154 with respect to the anchor element 152. With such rotation, the surgeon or other user could deploy the axisymmetric anchor element and confirm the anchor element's proper deployment (via direct or indirect viewing, e.g., radioscopy), and then rotate the sealing element to the desired rotational position, and then lock the sealing element at that desired position.

Figure 8E:
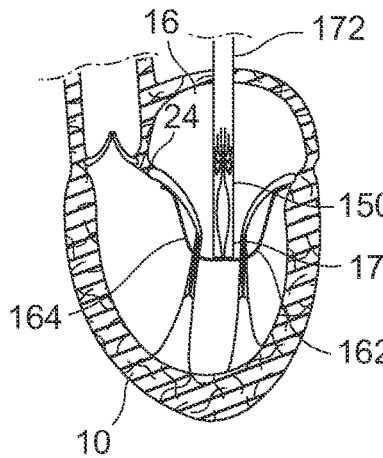
Figure 8F:
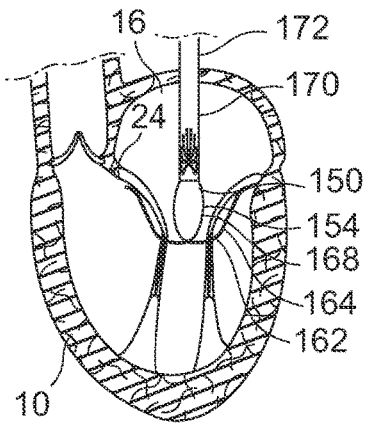
Figure 8G:
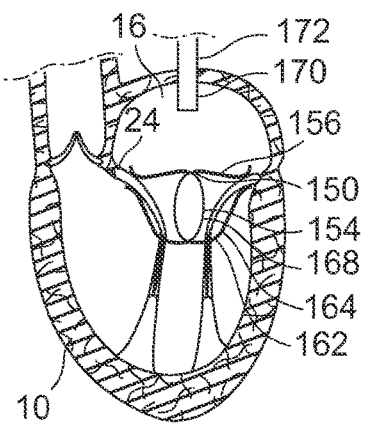

FIGS. 8D-8G depict side views of left atrium 16, left ventricle 18, mitral valve 24, and mitral valve annulus 25, with the device 150 at various stages of deployment therein according to an embodiment of the invention. The device 150 is secured within a distal end 170 of a delivery catheter 172, and the distal end 170 is advanced percutaneously or minimally-invasively into the mitral valve 24 of the patient via the left atrium 16 of the heart 10, as in FIG. 8D. In FIG. 8E, the ventricular anchor portion 166 is released from the catheter 172 and expanded into contact with heart tissue below the mitral valve 24. In FIG. 8F the sealing element 154 and central anchor portion 168 are positioned between the leaflets 42a, 42p of the mitral valve 24. At this point the sealing element 154 may be expanded, or expansion may not occur until after deployment of the atrial anchor portion 156. Although in FIG. 8F the sealing element is depicted as expanded, note that expansion thereof may occur after deployment of the atrial anchor portion. In FIG. 8G, atrial anchor portion 156 is expanded into contact with heart tissue above the mitral valve 24 as the device 150 is fully released from the catheter 172.

With the position and function of the device 150 confirmed (such as via radioscopy and/or other methods of remote viewing), the catheter 172 is then withdrawn from the patient. Although a percutaneous delivery via the atrial side is depicted, note that other deployment approaches are also within the scope of the invention, including transapical approaches.

Figure 9A:
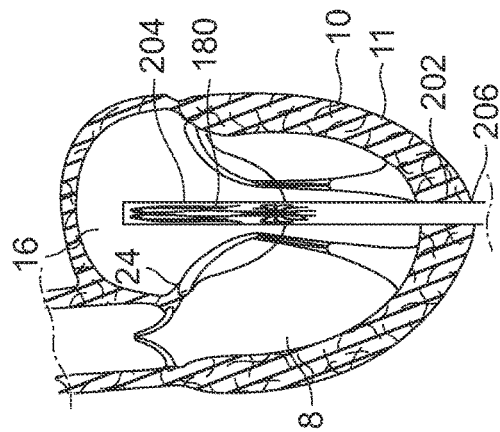
FIG. 9A depicts a side view of a device according to an embodiment of the invention.
Figure 9B:
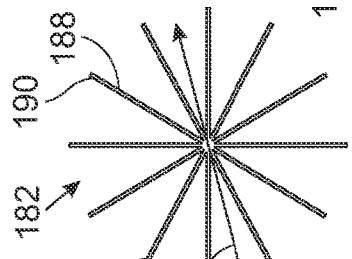
FIGS. 9B-9C depict top and bottom views, respectively, of a frame according to an embodiment of the invention.
Figure 9C:
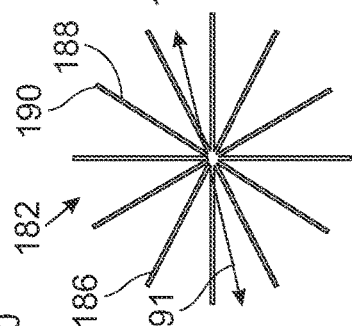
Figure 9D:
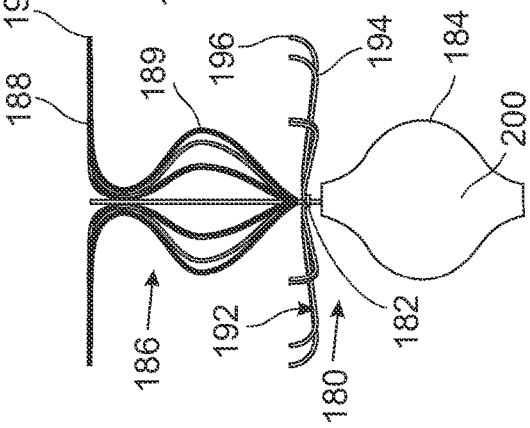
FIGS. 9D-9G depict side views of heart chambers with the device of FIG. 9A at various stages of deployment therein according to an embodiment of the invention.

FIG. 9A depicts a device 180 that is configured for deployment with anchor portions secured entirely in the atrium of a patient. An anchor element 182 anchors and supports a sealing element 184. The anchor element 182 has an upper atrial portion 186 with upper atrial arms 188 terminating in upper atrial arm distal ends 190. The upper atrial arms 188 are sized and configured to curve upward through the center of the atrium and outward to engage an upper surface of the atrium. The upper atrial arms 188 may include intermediate curves 189 that can act as shock absorbers, flexing and bending to permit the anchor element 182 to be compressed responsive to atrial shape changes as the heart beats. A lower atrial portion 192 has lower atrial arms 194 terminating in lower atrial arm distal ends 196. The lower atrial arms 194 may be sized and shaped to extend outward and across the lower portion of the atrium and engage the valvular annulus from the atrial side. Note that the anchor element 182 depicted may be axisymmetric when expanded in the absence of compressive or other distorting forces, so that during deployment the surgeon or other user does not have to worry about whether the anchor element 182 of the device 180 is rotated around its central axis to a proper deployment position with respect to the native valve and valve annulus. For example, when expanded without compressive/distorting forces (e.g., expanded in air), the anchor element 182 is symmetrical when viewed from above or below, as depicted in FIGS. 9B-9C. In the particular embodiment depicted, the expanded diameter 191 of the upper anchor element 186 is generally equal to the expanded diameter 197 of the lower anchor element 192, although other diameters are also within the scope of the invention. The upper anchor expanded diameter 191 and lower anchor expanded diameter may be in the range between 30 and 70 mm. Note that when expanded in an actual heart, the individual arms 188, 194 of the upper and lower anchor elements 186, 192 will be compressed or otherwise distorted by their interaction with the heart tissue, so that each arm may be contorted by the heart tissue into a shape slightly different from the shapes of other arms.

The anchor element 182 of FIG. 9A includes a sealing element support portion 200 which passes below the atrial portions 186, 192 and through the sealing element 184, and is configured to hold the sealing element 184 at a desired position within the native valve annulus after the other anchor portions 186, 192 have been deployed in the desired heart chamber, such as the left atrium 16 depicted. In the particular embodiment depicted, the sealing element support portion 200 corresponds to an axis of the sealing element 184 and an axis of the anchor element 182. The sealing element support portion 200 may be configured to act as a support frame for the sealing element 184, and/or may be configured to be shortened (e.g., by incorporating shortening mechanisms such as those in FIGS. 7A-7C) in order to effectuate shortening and thereby expansion of the sealing element 184. Note that the sealing element 184 in top profile (i.e., about its central axis) may be axisymmetric (e.g., circular) as in FIGS. 3E-H, or may be non-circular (e.g., elliptical) as in FIGS. 6A-6D. The sealing element 184, especially if it is non-circular/elliptical in top profile, may be configured for axial rotation (selective or responsive to body operation such as blood flow/valve operation) with respect to the anchor element 182, and a lock may be provided that can be activated to prevent further rotation of the sealing element 184 with respect to the anchor element 182. With such rotation, the surgeon or other user could deploy the axisymmetric anchor element and confirm the anchor element's proper deployment (via direct or indirect viewing, e.g., radioscopy), and then rotate the sealing element to the desired rotational position, and then lock the sealing element at that desired position.

Figure 9E:
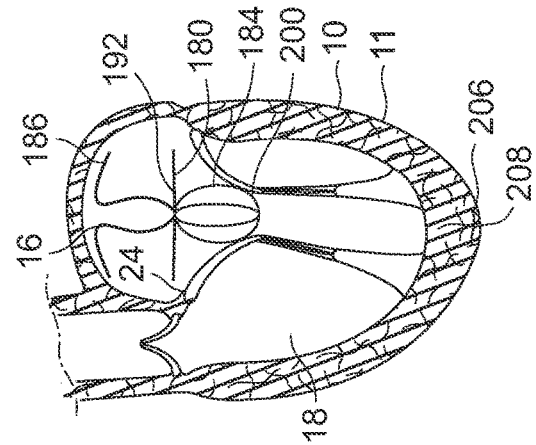
Figure 9F:
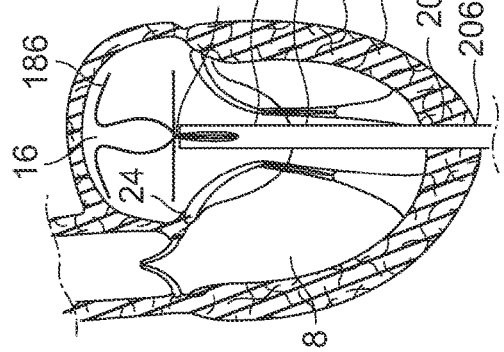
Figure 9G:
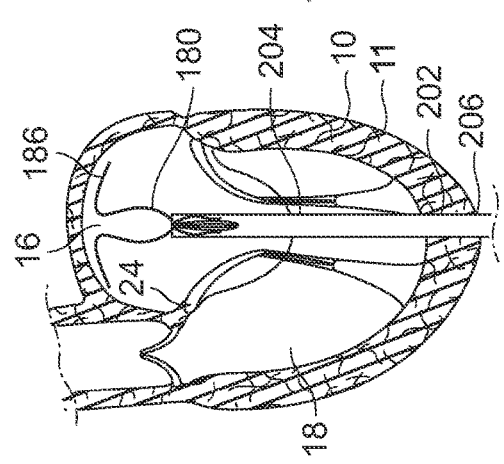

As depicted in FIGS. 9D-9G, the device 180 may be deployed via a transapical approach into the heart 10. The device 180 is secured within a distal end 204 of a delivery catheter 202, and the catheter distal end 204 is advanced via an opening 206 in the heart wall 11 (e.g., via an opening in a wall of the left ventricle 18, such as a transapical opening at the apex) and into the mitral valve 24 of the patient. In FIG. 9E, the upper atrial anchor portion 186 is expanded into contact with heart tissue toward the upper area of the left atrium 16 as the device 180 begins to be released from the catheter 202. In FIG. 9F the lower atrial anchor portion 192 is released from the delivery catheter 202 and expanded into contact with the lower portion of the atrium 16. FIG. 9G depicts the sealing element 184 and sealing element support portion 200 positioned between the leaflets of the mitral valve 24, and the sealing element 184 is expanded therebetween. The device 180 is fully released from the catheter 202. With the position and function of the device 180 confirmed (such as via radioscopy and/or other methods of remote viewing), the catheter 202 may then be withdrawn from the patient and the opening 206 closed via suture 208 and/or other methods/devices for closing openings.

Figure 10A:
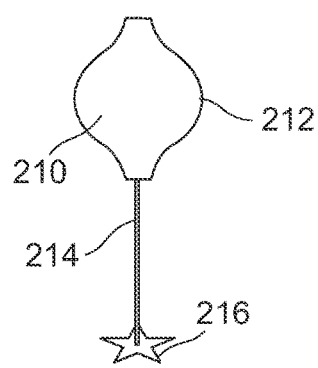
FIG. 10A depicts a side view of a device according to an embodiment of the invention.
Figure 10B:
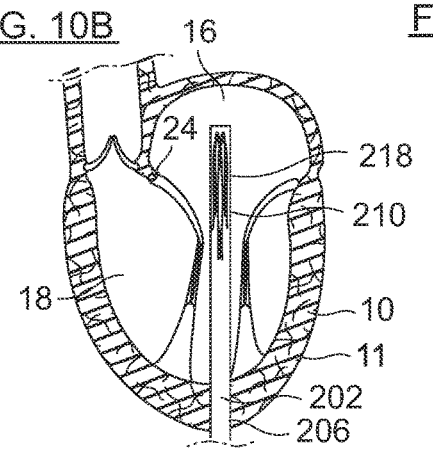
FIGS. 10B-10E depict side views of heart chambers with the device of FIG. 10 at various stages of deployment therein according to an embodiment of the invention.
Figure 10C:
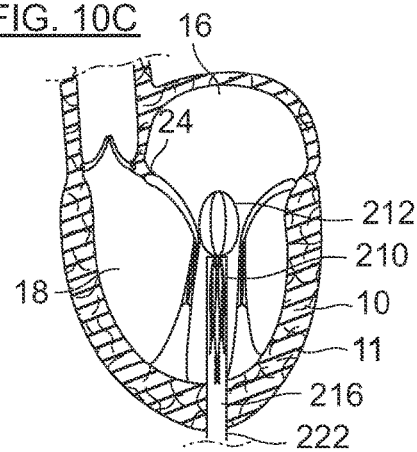
Figure 10D:
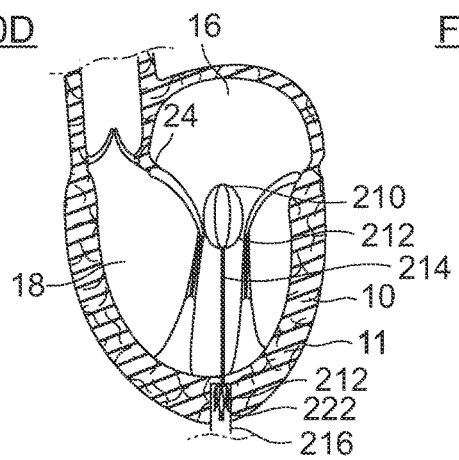
Figure 10E:
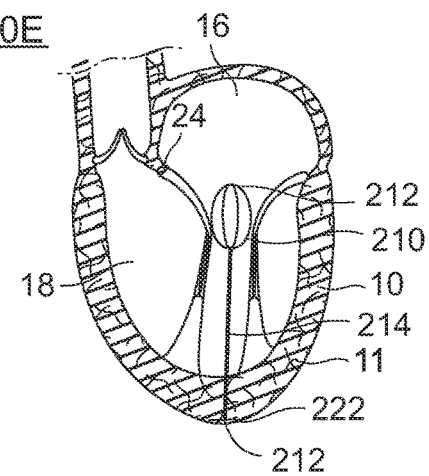

FIG. 10A depicts a device 210 having a sealing element 212 anchored via a tether 214 and anchor 216. The device 210 may be positioned in the distal end 218 of a delivery catheter 220 and advanced into the heart. In one embodiment, the device 210 is advanced transapically into the left ventricle 18 and to the mitral valve 24 via an opening 222 in the heart wall, where the opening 222 may be at the heart apex 19, as depicted in FIG. 10B. The sealing element 212 may be released from the catheter 216 at a position between the native valve leaflets 42a, 42p, as depicted in FIG. 10C. FIG. 10D depicts the catheter 220 withdrawn as the tether 214 is released from the catheter distal end 218, with the tether 214 being rigid or flexible depending on the desired application. As the catheter is removed from the heart 10, the anchor 216 is deployed in the heart wall 11, as shown in FIG. 10E. The user can then adjust the length of the tether 214 before locking the tether 214 to the anchor 216 at the desired length. Note that locking of the tether 214 to the anchor at the desired tether length can be achieved by known methods, such as via sliding locking mechanisms that initially allow the tether to slide through the lock but then prevent further movement, via knots in the tether line, etc.

Note that the sealing element 212 may be selectively expanded, fully or partially, at various times during deployment, such as when initially released from the delivery catheter; after the tether is extended; after the anchor is secured; or after the tether length is finalized. The tether length can also be adjusted at various times. For example, the sealing element 212 may be partially expanded when released from the catheter, with full expansion occurring just prior to or as the tether length is finalized in order to confirm proper sealing of the valve leaflets against the sealing element via radioscopy, etc. Although a transapical delivery via the ventricle and heart apex is depicted, note that other deployment approaches are also within the scope of the invention, including percutaneous approaches via blood vessels and/or the atrium side.

Figure 11A:
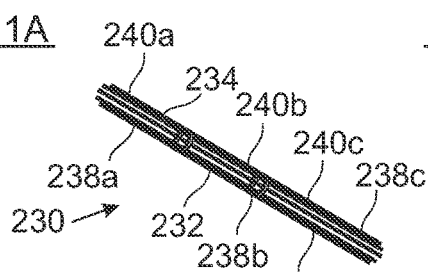
FIGS. 11A-11C depict perspective views of an anchor frame at with various portions expanded according to an embodiment of the invention.
Figure 11B:
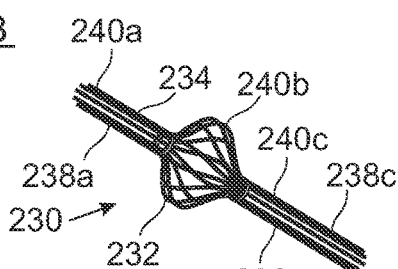
Figure 11C:
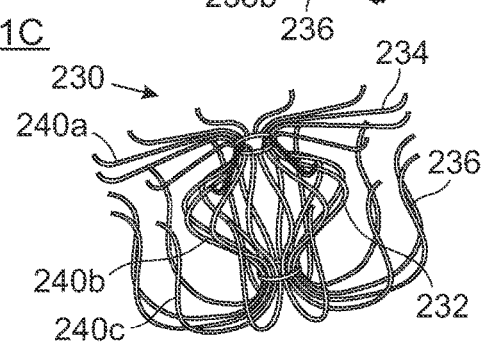
Figure 11D:
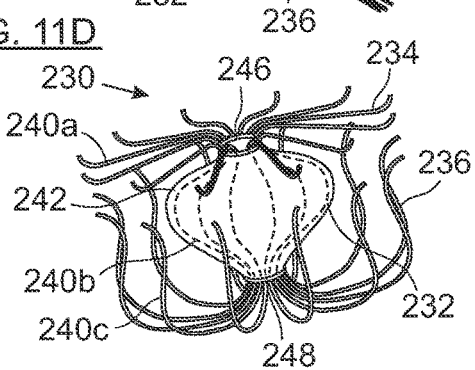
FIG. 11D depicts a device having the anchor element of FIGS. 11A-11C in an expanded configuration according to an embodiment of the invention.

An anchor frame 230 according to the invention may be formed of a memory material such as nitinol, and/or may have a central portion 232 configured to serve as a support frame for a sealing element. For example, as depicted in FIG. 11A, a frame 230 is formed as a generally tubular form of shape memory material with a central portion 232, upper portion 234, and lower portion 236, with each portion composed of slits 238a-c between rib-like elements 240a-c. The central portion 232 may be radially expanded into a desired shape by bending the rib-like elements 240b outward as depicted in FIG. 11B, and the desired shape can be set in the memory material via known methods. The upper and lower portions 234, 236 may similarly be formed to the desired shapes as in FIG. 11C, and the desired shapes set to the memory material. Note that the rib-like elements 240a-c are configured to extend out to form arms and other frame/anchor structures. The addition of a fluid-blocking covering 242 to the frame central portion 232 creates the sealing element 244. Note that the device may have a top opening 246 and/or a lower opening 248 in the sealing element portion, which permits some blood to flow into and out of the sealing element but avoids pooling of blood within it. Alternatively, one or both of the top and bottom of the sealing element portion may be entirely closed.

Anchor frames according to the invention may be formed of various biocompatible materials, including metals and polymers. For example, memory materials such as Nitinol may be used, thereby forming an anchor frame that can be compressed onto/into a catheter for minimally-invasive/percutaneous delivery and then will expand to its "memorized" shape upon release from the catheter. Non-memory materials such as stainless steel or cobalt chromium are also within the scope of the invention. The anchor frame may include a biocompatible covering, such as of a Dacron or other fabric. The biocompatible covering may encourage tissue ingrowth to promote tissue anchoring. The biocompatible covering may alternatively resist tissue ingrowth.

Sealing elements according to the invention may be formed of various biologically compatible materials, including metals, fabrics, plastics, and tissue. Some materials that may be used for such sealing elements include materials currently used in forming leaflets of prosthetic heart valves. For example, synthetic materials (e.g., polymers such as thermoplastic elastomers or resins, including polyurethane and silicone, etc.), natural/treated tissue (e.g., valve leaflet tissue, bovine or equine pericardium, etc.), fabrics (e.g., Dacron), etc. may be used.

Sealing elements may preferably wrap around the exterior and/or interior of any anchor portions that serve to directly support or frame the sealing element, so that any wireform/ rib-like elements of the support frame portion are covered and/or encapsulated by the sealing element material in order to prevent the native valve leaflets from contacting any frame elements of the sealing element support frame, etc.

During deployment of a device according to the invention, such as the deployment procedures depicted in FIGS. 8D-8G or 9D-9G or 10B-10E, the surgeon or other user may controllably expand the sealing element to a desired diameter/length, or the sealing element may be configured to self-expand to a pre-set configuration such as upon release from the delivery catheter. For example, if the sealing element comprises a memory-material (e.g., nitinol) support frame, that support frame may automatically expand to a pre-set memory material configuration (length/diameter) upon release from radial constraints such as a delivery lumen of the delivery catheter. Alternatively, the surgeon or other user may actively control the expansion of the sealing element to a specifically selected diameter/length, such as by activating length/diameter adjusting elements such as those depicted in FIGS. 7A-7C. Before, during, and/or after sealing element expansion, the surgeon/user may actively monitor heart valve function and/or leaflet coaptation (with the sealing element) and/or sealing element position/size via various techniques, such as fluoroscopy or other visualization techniques (including the use of radiopaque markers on the sealing element). The surgeon/user may select the final diameter/length of the sealing element based on the information on heart valve function and/or leaflet coaptation. The surgeon/user may also selectively rotate the sealing element about its central axis with respect to the support anchor (before, during, or after deployment of the support anchor) in order to better position the sealing element between the native valve leaflets, such as where the sealing element has an elliptical top profile as depicted in FIGS. 6A-6D. For example, with such an elliptical profiled sealing element, the user may deploy the anchor element, then rotate the sealing element (expanded or unexpanded) with respect to the anchor element and native valve in order to position the minor diameter to extend generally perpendicular to the anterior and posterior mitral valve leaflets, and to position the major diameter to extend between the valve commissural points. Once the desired rotational position is achieved, the sealing element can be locked in that position.

If the user (e.g., surgeon or other medical staff) is not satisfied with the initial positioning of all or part of the device, the device or parts thereof may be withdrawn (completely or partially) into the catheter and then re-deployed at the desired position. For example, if after initial deployment the sealing element is positioned too high or too low with respect to the mitral valve leaflets, the device or parts thereof can be at least partially withdrawn into the catheter and then re-deployed at a position higher or lower than the previous position. Similarly, if the user is not satisfied with the deployed size of the sealing element, he/she can adjust the length/radius of the sealing element until the desired sealing/coaptation with the native leaflet is achieved. Also, for sealing elements that are non-circular/elliptical in top profile, the user can modify the rotational position of the sealing element to a desired rotational position that may optimize valve function.

Radiopaque markers or other visibility-enhancing markers may be included with the device in order to make the device and key elements thereof more clearly visible when the device is deployed or inspected using fluoroscopy or other visualization techniques. For example, enhanced visibility markers such as radiopaque markers may be secured to portions of the sealing element and/or the anchor elements, etc.

Note that FIGS. 3B-3D, 8E, 9A, and 11A-11D are computer-generated to-scale drawings where dimensions are to scale within each drawing. All dimensions listed are by way of example, and devices according to the invention may have dimensions outside those specific values and ranges. Although in some of the drawings the sealing element material is depicted as extending between frame portions but with the frame portions uncovered, in various embodiments of the invention (including each of the embodiments of the invention depicted in the drawings) the sealing element material may preferably wrap around the exterior and/or interior of the support frame portions, so that the wireform/rib-like frame elements are covered and/or encapsulated by sealing element material in order to prevent the native valve leaflets from contacting any frame element.

Although the specific embodiments discussed above are directed toward mitral valve repair, the invention may also be applicable for use in repairing other heart valves, including the aortic, tricuspid, and pulmonary valves.

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A sealing element configured for anchoring between native valve leaflets to improve valve function, the sealing element comprising:
   a mesh support frame comprising a delivery configuration and an expanded configuration, wherein in the delivery configuration the mesh support frame is substantially tubular with a delivery diameter, and wherein in the expanded configuration the mesh support frame is radially expanded to an expanded central diameter at a center portion thereof while end portions of the mesh support frame remain in the delivery diameter, wherein the expanded diameter is at least twice the delivery diameter;
   a covering over the mesh support frame, wherein the covering inhibits passage of blood therethrough;
   an anchor member comprising an atrial portion configured to engage an atrial side of the valve and a ventricular portion configured to engage a ventricular portion of the valve; and
   wherein the sealing element is configured to block flow therethrough in both diastole and systole.

2. The sealing element of claim 1, wherein the expanded central diameter is at least three times the delivery diameter.

3. The sealing element of claim 1, wherein the expanded central diameter is at least five times the delivery diameter.

4. The sealing element of claim 1, wherein the sealing element in the expanded configuration comprises an axisymmetrical top profile.

5. The sealing element of claim 1, wherein the sealing element in the expanded configuration comprises an elongated top profile.

6. The sealing element of claim 1, wherein the sealing element in the expanded configuration comprises an elliptical top profile.

7. The sealing element of claim 1 wherein the mesh support frame comprises a shape having varying radial dimensions around a circumference of the frame.

\* \* \* \* \*